(12) United States Patent
Myers

(10) Patent No.: US 8,998,907 B2
(45) Date of Patent: Apr. 7, 2015

(54) SYSTEM AND METHOD FOR A MODULAR RESECTION GUIDE

(71) Applicant: Reese Myers, Columbia City, IN (US)

(72) Inventor: Reese Myers, Columbia City, IN (US)

(73) Assignee: Symmetry Medical Inc, Warsaw, IN (US)

( * ) Notice: Subject to any disclaimer, the term of this patent is extended or adjusted under 35 U.S.C. 154(b) by 168 days.

(21) Appl. No.: 13/677,442

(22) Filed: Nov. 15, 2012

(65) Prior Publication Data

US 2013/0165936 A1 Jun. 27, 2013

Related U.S. Application Data

(60) Provisional application No. 61/563,075, filed on Nov. 23, 2011.

(51) Int. Cl.
*A61F 5/00* (2006.01)
*A61B 17/14* (2006.01)
*A61B 17/17* (2006.01)
*A61B 17/15* (2006.01)

(52) U.S. Cl.
CPC ............... *A61B 17/14* (2013.01); *A61B 17/17* (2013.01); *A61B 17/15* (2013.01); *A61B 17/151* (2013.01); *A61B 17/155* (2013.01)

(58) Field of Classification Search
CPC .......... A61B 17/1742; A61B 17/1746; A61B 17/175; A61B 17/1753; A61B 17/1764; A61B 17/1767; A61B 17/154; A61B 17/155; A61B 17/157; A61B 17/158; A61B 17/56; A61F 2/38; A61F 2/3859; A61F 2/389
USPC ....................................... 606/86 R, 87, 88, 89
See application file for complete search history.

(56) References Cited

U.S. PATENT DOCUMENTS

| | | |
|---|---|---|
| 2004/0215203 A1* | 10/2004 | Michelson ...................... 606/96 |
| 2005/0154394 A1 | 7/2005 | Michalowicz |
| 2010/0217338 A1 | 8/2010 | Carroll et al. |
| 2011/0106093 A1 | 5/2011 | Romano et al. |
| 2011/0218541 A1* | 9/2011 | Bailey et al. ..................... 606/88 |
| 2011/0245835 A1 | 10/2011 | Dodds et al. |
| 2013/0096680 A1* | 4/2013 | Ribeiro et al. ............. 623/14.12 |

* cited by examiner

*Primary Examiner* — Sameh Boles
(74) *Attorney, Agent, or Firm* — AKC Patents LLC; Aliki K. Collins

(57) ABSTRACT

A modular bone resection guide system includes a positioning base configured to be attached to a bone, a modular resection block configured to be removably attached to various locations of the positioning base and a cutting tool configured to be supported and guided by the modular resection block while cutting the bone.

6 Claims, 4 Drawing Sheets

SYSTEM AND METHOD FOR A MODULAR RESECTION GUIDE

CROSS REFERENCE TO RELATED CO-PENDING APPLICATIONS

This application claims the benefit of U.S. provisional application Ser. No. 61/563,075 filed on Nov. 23, 2011 and entitled SYSTEM AND METHOD FOR A MODULAR RESECTION GUIDE which is commonly assigned and the contents of which are expressly incorporated herein by reference.

FIELD OF THE INVENTION

The present invention relates to a system and a method for a modular resection guide, and in particular, to an osteotomy resection guide that includes a positioning base and a modular resection block.

BACKGROUND OF THE INVENTION

In several bone pathologies, bone resection is applied. Typically, bone resections are made using saws or milling devices. Accuracy in the bone resection operation is critical for reducing neighboring tissue damage and excessive bleeding and for limiting the amount of the resected bone. Accuracy in the bone cutting operation is also required in the preparation of a bone contour for receiving prosthesis. In order to perform accurate cuts with these cutting instruments, surgeons utilize cutting guide blocks. These cutting guide blocks include guiding surfaces or slots and the cutting instruments are aligned with the cutting surfaces or slide within a slot in order to perform an accurately positioned bone incision. The fabrication of cutting surfaces and slots in the cutting guide blocks requires high precision manufacturing, and therefore is time consuming and expensive. Furthermore, the locations of these slots and surfaces are fixed and their dimensions, shapes and position cannot be changed or rearranged in order to accommodate patients with different anatomies and in order to perform resections in different anatomic locations or resections that prepare the bone contour for receiving different type of prostheses.

Accordingly, there is a need for a low cost cutting guide block and in particular for a cutting guide block that provides flexibility and modularity in the bone cutting process.

SUMMARY OF THE INVENTION

The present invention provides a modular resection guide that includes a positioning base, a modular resection block and a saw blade.

In general, in one aspect, the invention features a modular bone resection guide system including a positioning base configured to be attached to a bone, a modular resection block configured to be removably attached to various locations of the positioning base and a cutting tool configured to be supported and guided by the modular resection block while cutting the bone.

Implementations of this aspect of the invention may include one or more of the following features. The positioning base includes a parallelepiped body having a central through-opening and a plurality of peripheral openings surrounding the central through opening. The modular resection block includes a parallelepiped body having a first slot extending from a front surface to a back surface of the parallelepiped body and the first slot is shaped and dimensioned to slidably support and guide the cutting tool. The modular resection block further includes first and second pins and the modular resection block is removably attached to the positioning base by inserting the first and second pins into first and second peripheral openings of the positioning base, respectively. The system further includes a fastening screw configured to secure the position of the cutting tool relative to the modular resection block. The cutting tool comprises a saw blade and the saw blade includes an elongated body extending along a first direction and having a rounded proximal end and a straight distal end. The distal end has saw teeth. The elongated body of the saw blade further has an elongated slot extending along the first direction and the modular resection block further includes an elongated second slot being perpendicular to the first slot and extending along a second direction. The second direction intersects the first direction at a first location and the fastening screw is inserted into the first location and secures the position of the saw blade relative to the modular resection block. The rounded proximal end includes a through opening shaped and dimensioned to support a power tool. The positioning base includes an outer surface contoured to fit the bone's surface anatomy. The cutting tool may be one of knifes, scissors, milling devices, drills, or blades.

In general, in another aspect, the invention features a method for a modular bone resection including the following: First providing a positioning base and attaching the positioning base to a bone, Next, providing a modular resection block and removably attaching the modular resection block to various locations of the positioning base. Next, providing a cutting tool and supporting and guiding the cutting tool by the modular resection block while cutting the bone.

Among the advantages of this invention may be one or more of the following. The modular design of the present invention reduces the overall cost of the traditional cutting block by removing the necessity for multiple slots. The cutting block slots are costly due to tight positional and feature tolerances. Additionally, the overall weight of the system is reduced, which makes it easier for the surgeon to handle the device during surgery. Overall, the duration of the surgery may be reduced. The cutting accuracy of the bone is improved and potential complications due to excessive bleeding because of inaccurate cuttings are avoided. The modularity of the position base design and the cutting block design allows a quick and easy development of a custom resection system for each patient, for each anatomic location and for each type of prostheses.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

The present invention provides a modular resection guide that includes a positioning base, a modular resection block and a saw blade.

Figure 1:
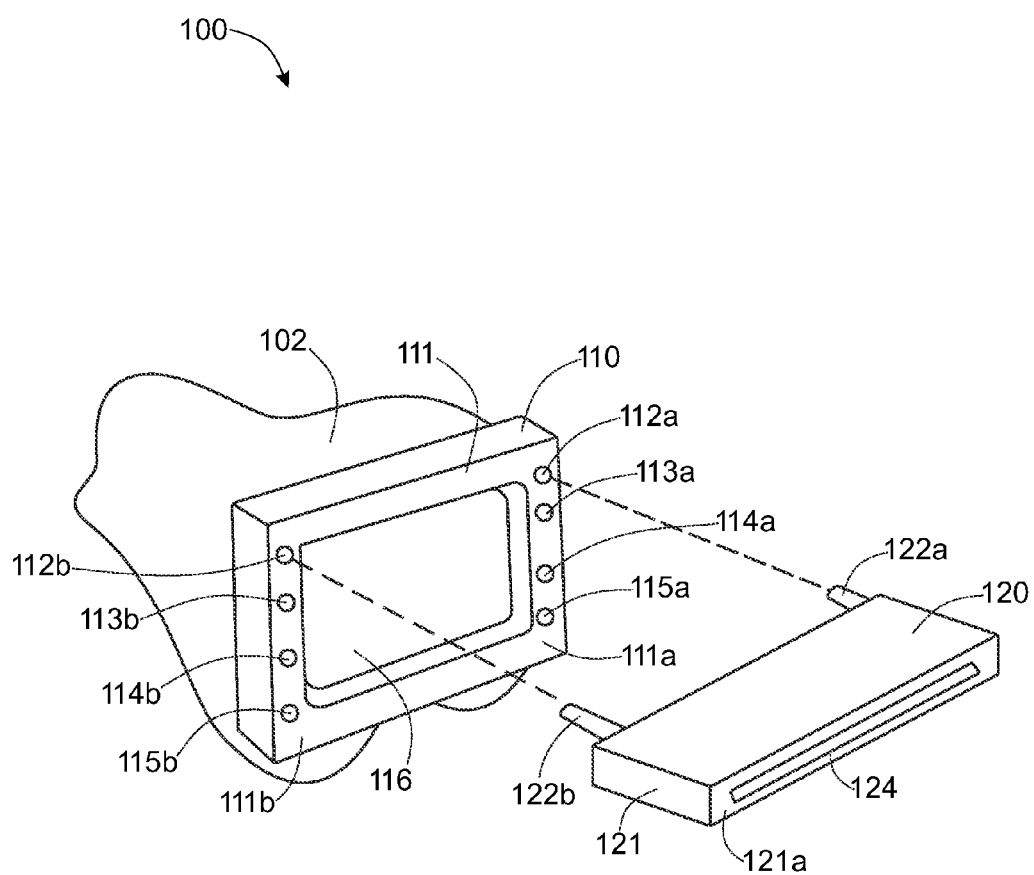
FIG. 1 is a schematic diagram of a modular resection guide system of this invention.
Figure 2:
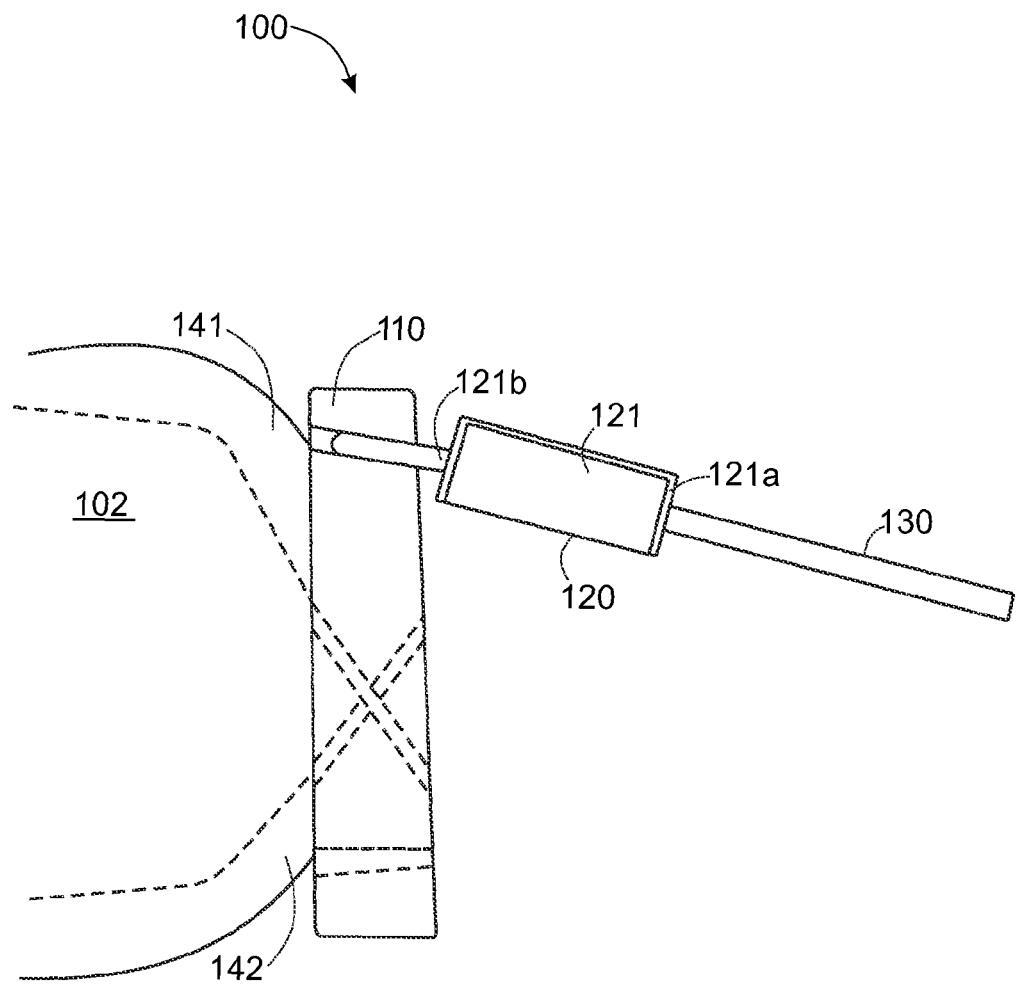
FIG. 2 is side view of the modular resection guide system of FIG. 1.

Referring to FIG. 1, a modular resection guide system 100 includes a positioning base 110, and a modular resection block 120. Positioning base 110 is attached to a bone 102 and the modular resection block 120 is configured to be attached to various locations of the positioning base 110. Positioning base 110 includes a rectangular parallelepiped body 111 that has a central through opening 116 and apertures 112a, 113a, 114a, 115a arranged on the right front side 111a and apertures 112b, 113b, 114b, 115b arranged on the left front side 111b. Opening 116 extends from the front side to the backside of the body 111. Apertures 112a, 113a, 114a, 115a are arranged linearly from the top to the bottom of body 111. Similarly apertures 112b, 113b, 114b, 115b are arranged linearly from the top to the bottom of body 111. The number and geometric arrangement of apertures 112a, 113a, 114a, 115a and 112b, 113b, 114b, 115b varies in order to accommodate modular resection blocks 120 with different geometries and in order to position the modular resection block 120 in different locations of the positioning base 110. Modular resection block 120 includes a rectangular parallelepiped body 121 that has a slot 124 extending from its front surface 121a to the back surface 121b, as shown in FIG. 2. Modular resection block 120 also includes pins 122a, 122b extending from its back surface 121b, as shown in FIG. 1 and FIG. 2. Pins 122a, 122b are aligned with apertures 112a and 112b and are inserted into apertures 112a and 112b, respectively. This alignment and insertion of the pins 122a, 122b into apertures 112a, 112b results in positioning the modular resection block 120 at a first location of the positioning base 110 near the top, as shown in FIG. 2. A saw blade 130 is inserted into the slot 124 from the front side 121a of the resection block 120 and is used to cut a first opening 141 into a first location of the bone 102. Once the cut is completed in this first location, the resection block 120 is removed and then placed in a second location of the positioning base 110. In one example, the resection block pins 122a, 112b are aligned with the apertures 115a, 115b of the positioning based 110, respectively, in order to position the resection block 120 in a second location of the position base 110 near the bottom. Saw blade 130 is then inserted into the slot 124 from the front side 121a of the resection block 120 and is used to cut a second opening 142 into a second location of the bone 102.

Figure 3:
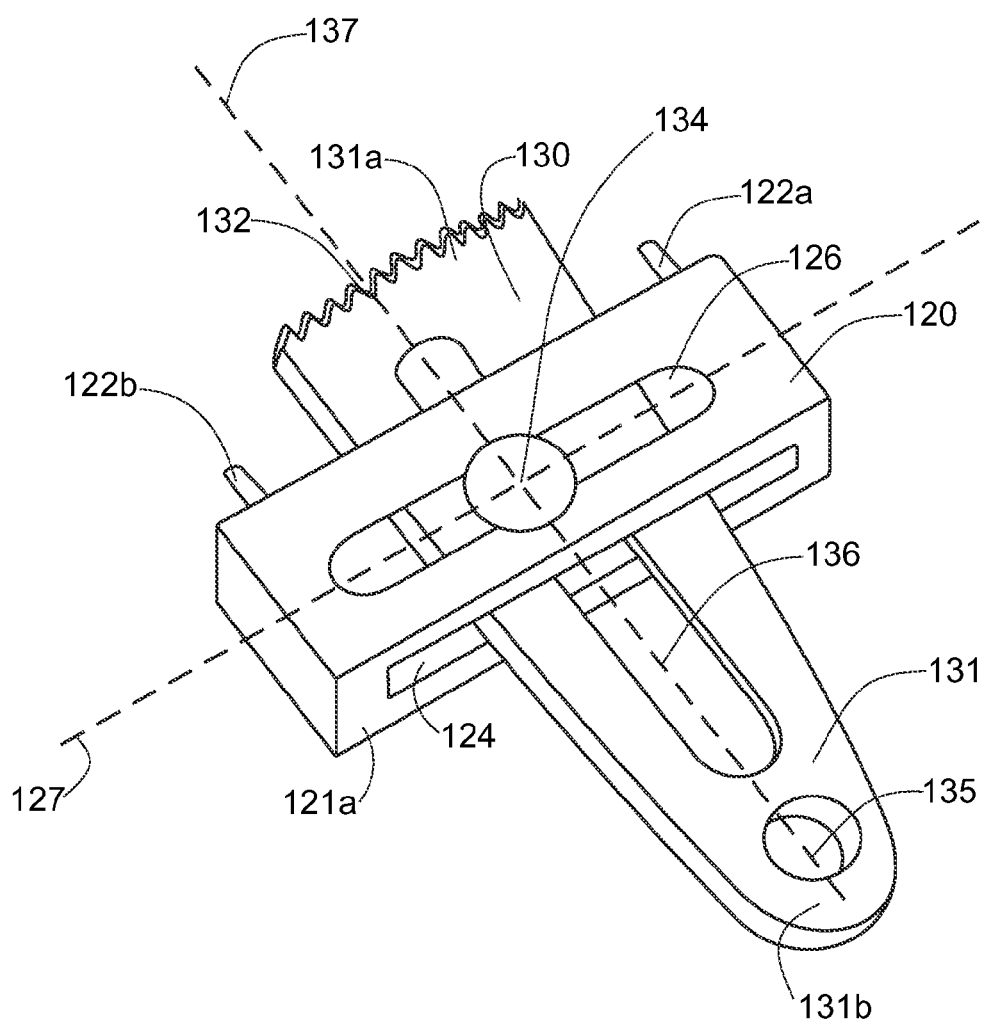
FIG. 3 is a front perspective view of a saw blade inserted and secured in the modular resection block of FIG. 1.

In another embodiment, saw blade 130 and modular resection block 120 are attached to each other and form a single unit. Referring to FIG. 3, saw blade 130 is slidably attached to modular resection block 120. Saw blade 130 includes an elongated body 131 extending along elongated axis 137 and having a rounded conical back end 131b and a straight front-end 131a. Front-end 131a includes saw teeth or serrations 132 used to cutting out openings in the bone. Body 131 also includes an elongated opening 136 extending also along axis 137 and a round opening 135 near the back end 135. Round opening 135 is used for connecting to a power tool. In this embodiment, modular resection block 120 includes an elongated opening 126 extending along axis 127, which is arranged perpendicular to axis 137. Saw blade 130 is inserted into slot 124 from the front side 121a of the resection block 120 and is configured to slide within slot 124 along axis 137. The two elongated slots 136 and 126 are arranged perpendicular to each other and a fastening screw 134 is used to secure their relative position.

Figure 4:
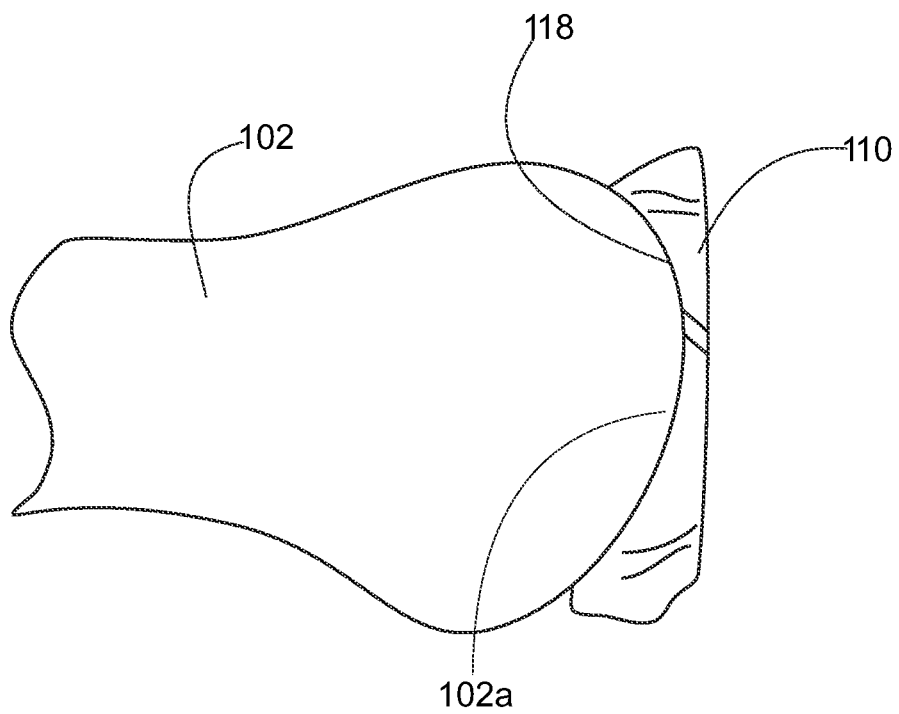
FIG. 4 is a side view of a positioning base that conforms to the patient's bone anatomy.

In some embodiments, positioning base 110 is designed to fit the contour of the specific surface anatomy of the bone to which it is attached. Referring to FIG. 4, the surface anatomy of bone 102 is determined via an X-ray computed tomography (CT) scan of the patient's bone and then the back surface 118 of position block 110 is cutout or molded to complement the bone surface 102a. This design of the positioning base 110 provides a more secure attachment and alignment of the positioning base 110 to the bone 102 and results in better accuracy of the bone cutting.

Other embodiments include the following, among others. Knifes, scissors, milling devices, drills and blades with different designs may be used instead of a saw blade.

The system of this invention may be used in total knee replacement (TKR) surgery, for resection of the femoral neck during hip arthroplasty, for resection of the distal tibia during ankle arthroplasty, for resection of the distal radius during wrist arthroplasty, for resection of the proximal humerus during shoulder arthroplasty and for various corrective osteotomies.

Several embodiments of the present invention have been described. Nevertheless, it will be understood that various modifications may be made without departing from the spirit and scope of the invention. Accordingly, other embodiments are within the scope of the following claims.

What is claimed is:

1. A modular bone resection guide system comprising:
   a positioning base configured to be attached to a bone;
   a modular resection block configured to be removably attached to various locations of the positioning base;
   a cutting tool configured to be supported and guided by the modular resection block while cutting the bone;
   wherein the modular resection block comprises parallelepiped body having a first slot extending from a front surface to a back surface of the parallelepiped body and wherein said first slot is shaped and dimensioned to slidably support and guide the cutting tool;
   wherein the cutting tool comprises a saw blade and wherein the saw blade comprises an elongated body extending along a first direction and having a rounded proximal end and a straight distal end and wherein the distal end comprises saw teeth;
   wherein the elongated body of the saw blade further comprises an elongated slot extending along the first direction and wherein the modular resection block further comprises an elongated second slot perpendicular to said first slot and extending along a second direction and wherein said second direction intersects said first direction at a first location and wherein a fastening screw is inserted into said first location and secures the position of the saw blade along the second direction relative to the modular resection block, while allowing the saw blade to slide along the first direction within the first slot of the modular resection block.

2. The system of claim 1, wherein the positioning base comprises a parallelepiped body having a central through-opening and a plurality of peripheral openings surrounding said central through opening.

3. The system of claim 2, wherein the modular resection block further comprises first and second pins and wherein said modular resection block is removably attached to the positioning base by inserting the first and second pins into first and second peripheral openings of the positioning base, respectively.

4. The system of claim 1, wherein said rounded proximal end comprises a through opening shaped and dimensioned to support a power tool.

5. The system of claim 1, wherein the positioning base comprises an outer surface contoured to fit the bone's surface anatomy.

6. The system of claim 1, wherein the cutting tool comprises one of knifes, scissors, milling devices, drills, or blades.

* * * * *